(12) United States Patent
Fanselow et al.

(10) Patent No.: US 7,880,471 B2
(45) Date of Patent: Feb. 1, 2011

(54) ADAPTER FOR SUPPLYING ELECTROLYTE TO A POTENTIOMETRIC SENSOR

(75) Inventors: Christian Fanselow, Geringswalde (DE); Lothar Auerswald, Döbeln (DE)

(73) Assignee: Endress + Hauser Conducta Gesellschaft fur Mess-und Regeltechnik mbH + Co. KG, Gerlingen (DE)

(*) Notice: Subject to any disclaimer, the term of this patent is extended or adjusted under 35 U.S.C. 154(b) by 548 days.

(21) Appl. No.: 11/792,407

(22) PCT Filed: Nov. 25, 2005

(86) PCT No.: PCT/EP2005/056219
§ 371 (c)(1),
(2), (4) Date: May 20, 2008

(87) PCT Pub. No.: WO2006/061327
PCT Pub. Date: Jun. 15, 2006

(65) Prior Publication Data
US 2009/0096458 A1    Apr. 16, 2009

(30) Foreign Application Priority Data
Dec. 6, 2004   (DE) .................. 10 2004 058 863

(51) Int. Cl.
*G01N 27/42*    (2006.01)
*G01N 27/416*   (2006.01)
*G01N 27/28*    (2006.01)
*G01D 21/00*    (2006.01)

(52) U.S. Cl. .................. 324/425; 324/438; 324/450; 73/866.5

(58) Field of Classification Search .................. 324/425, 324/438, 450
See application file for complete search history.

(56) References Cited

U.S. PATENT DOCUMENTS 4,176,032 A * 11/1979 Stevenson, Jr. .............. 204/415

(Continued)

FOREIGN PATENT DOCUMENTS

DE    1 914 266    1/1970

(Continued)

OTHER PUBLICATIONS

JUMO: Datasheet 20.2900 "Jumo Measuremnet and Control", Aug. 1998, pp. 1-21 XP 002363597.

*Primary Examiner*—Jeff Natalini
(74) *Attorney, Agent, or Firm*—Bacon & Thomas, PLLC

(57) ABSTRACT

An adapter for a potentiometric sensor having a sensor shaft, which has a reference liquid opening in its exterior surface. The adapter comprises an annular chamber member having a sensor opening for receiving the sensor shaft. Arranged in the sensor opening are first and second sealing rings for the sensor shaft. The axial position of the reference liquid opening lies between the first and second sealing rings. Formed between the sealing rings and the sensor shaft is an annular chamber, which is in communication with the reference liquid opening. The annular chamber member further includes a duct extending between the annular chamber and a reference feed opening. The adapter further includes a process connection member having a process connection opening, which surrounds the sensor shaft, and whose axis is aligned with the axis of the sensor opening. The axial position of the process connection member is fixed relative to the annular chamber member, and the process connection member is freely rotatable relative to the annular chamber member.

11 Claims, 2 Drawing Sheets

U.S. PATENT DOCUMENTS

| | | | |
|---|---|---|---|
| 4,383,908 A * | 5/1983 | Phelps et al. | 204/409 |
| 5,553,794 A * | 9/1996 | Oliver et al. | 241/36 |
| 6,926,814 B2 * | 8/2005 | Koenemann et al. | 204/409 |
| 2004/0194563 A1 | 10/2004 | Milanovic | |
| 2008/0196516 A1 * | 8/2008 | Kimonides | 73/864.63 |

FOREIGN PATENT DOCUMENTS

| | | |
|---|---|---|
| DE | 31 18 447 A1 | 11/1982 |
| DE | G 89 14 571.2 | 5/1990 |
| DE | 195 25 913 A1 | 1/1997 |
| DE | 296 16 725 U1 | 1/1997 |
| DE | 199 53 218 A1 | 5/2001 |
| DE | 101 37 115 A1 | 2/2003 |
| DE | 102 56 649 A1 | 5/2004 |
| EP | 0 279 541 | 8/1988 |
| EP | 0 541 739 B1 | 5/1993 |
| EP | 1 464 951 A2 | 11/2004 |

* cited by examiner

ADAPTER FOR SUPPLYING ELECTROLYTE TO A POTENTIOMETRIC SENSOR

TECHNICAL FIELD

The present invention relates to sensors requiring a liquid substance as a reference- or calibration-solution. Such sensors include, for example, potentiometric sensors, especially pH-sensors or redox-sensors. The invention will be explained with reference to these examples, but it is not limited thereto.

BACKGROUND DISCUSSION

Potentiometric sensors usually measure potential difference between a working electrode and a reference electrode, with the working electrode being arranged in a buffer solution, which is separated by a glass membrane from the medium to be investigated. The reference electrode is placed in a reference electrolyte; in the case of a pH-sensor, the reference electrolyte can be a 3.5 molar KCl-solution.

For assuring constant quality of measurement, the reference electrolyte must be renewed at appropriate times. To this end, pH- or redox-sensors usually have a replenishment opening on their exterior surface. Replenishment of the reference electrolyte proves to be cumbersome, in so far as operating personnel must go to each sensor individually, in order to perform replenishment through its replenishment opening. For facilitating this procedure, pH-sensors are available, which have a tube connection, via which reference electrolyte can flow-in from a reservoir. The tube connection can be, for example, a tube-nipple of glass on the replenishment opening, or it can be integrated into a sensor head. Similarly, the Jumo company offers a so-called pressure head, which has a tube connection for the reference electrolyte.

All of the described sensors are, in accordance with their use, screwed into a process opening. As this happens, a sealing ring, as process seal, is compressed between sealing surfaces on the sensor and on the process opening. Associated with this prior art is, however, a safety risk in respect that an extra rotation of the tube connection with respect to the process opening, for instance for bringing the tube connection into the right orientation, can lead to an over-tightening of the process seal.

Additionally, the pressure head of the Jumo company has the following safety deficiency. A sealing ring, which seals the path of the reference liquid feed against the shaft of the sensor externally of the path, is pressed by means of a screw-in sleeve into its sealing seat and against the sensor shaft. The screw-in sleeve is threaded at both ends. A first thread serves for screwing the screw-in sleeve into the sensor head, for compressing the sealing ring in the described manner. The second thread serves as the process connection thread, for screwing the sensor into a process connection. A turning of the sensor head thus endangers, in this case, two seals, namely the process seal and the seal of the reference liquid feed. In an extreme case wherein both seals would fail, it is then possible for reference liquid to get into the process medium which is being measured.

SUMMARY OF THE INVENTION

An object of the present invention, therefore, is to provide a potentiometric sensor having an electrolyte connection, as well as an adapter with an electrolyte connection for potentiometric sensors, which overcome the disadvantages of the state of the art.

The object is achieved according to the invention by an adapter, comprising: an axisymmetric sensor shaft, which has a reference liquid opening in its exterior surface; an annular chamber member having an axisymmetric sensor opening for receiving the axisymmetric sensor shaft in a predetermined axial position relative to the annular chamber member; the sensor opening having a first annular seal-seat in a first axial section and a second annular seal-seat in a second axial section; a first sealing ring and a second sealing ring situated between the first seal-seat and the sensor shaft and between the second seal-seat and the sensor shaft, the first and the second sealing rings adapted to be clamped; a process connection member having a process connection opening, which surrounds the sensor shaft, and whose axis is aligned with the axis of the sensor opening; wherein: the axial position of the reference liquid opening lies between the first and second axial sections, when the sensor shaft is properly positioned in the adapter, so that, between the first and second sealing rings and the exterior surface of the sensor shaft, an annular chamber is formed, which is in communication with the reference liquid opening; the annular chamber member further having a duct, which extends between the annular chamber and a reference feed opening; and the axial position of the process connection member is fixed relative to the annular chamber member, and the process connection member is freely rotatable relative to the annular chamber member, and the potentiometric sensor, comprising: an axisymmetric, sensor shaft, which has a reference liquid opening in its exterior surface; an annular chamber member having an axisymmetric, sensor opening into which the sensor shaft is received in a predetermined axial position relative to the annular chamber member; and a process connection member having a process connection opening, which surrounds the sensor shaft, and whose axis is aligned with the axis of the sensor opening, wherein: the sensor opening has a first annular seal to the sensor shaft in a first axial section and a second annular seal to the sensor shaft in a second axial section; the axial position of the reference liquid opening lies between the first and the second axial sections, when the sensor shaft is properly placed in the adapter, so that, between the first and second seals and the external surface of the sensor shaft, an annular chamber is formed, which is in communication with the reference liquid opening; the annular chamber member further includes a duct, which extends between the annular chamber and a reference feed opening; and the axial position of the process connection member relative to the annular chamber member is fixed, and the process connection member is freely rotatable relative to the annular chamber member.

The adapter of the invention for a potentiometric sensor having an axisymmetric sensor shaft, which has a reference liquid opening in its exterior surface, includes an annular chamber member having an axisymmetric sensor opening for accommodating the sensor shaft in a predetermined axial position with reference to the annular chamber member, wherein the sensor opening has a first annular seal-seat in a first axial section and a second annular seal-seat in a second axial section, between the first seal-seat and the sensor shaft and between the second seal-seat and the sensor shaft, first and second sealing rings can be clamped, the axial position of the reference liquid opening lies between the first and second axial sections, when the sensor shaft is properly positioned in the adapter, so that, between the first and second sealing rings and the exterior surface of the sensor shaft, an annular chamber is formed, which in communication with the reference liquid opening, and the annular chamber member further includes a duct extending between the annular chamber and a reference feed opening, characterized in that the adapter further includes a process connection member having a process connection opening, which surrounds the sensor shaft, and whose axis is aligned with the axis of the sensor opening, wherein the axial position of the process connection member is fixed relative to the annular chamber member, and the process connection member is freely rotatable relative to the annular chamber member.

The first seal-seat can include, for example, a first sealing surface for a sealing ring, bordering on a first end section of the sensor opening and facing such. In the first end section of the sensor opening, a thread can be provided, into which a complementary thread, which is provided, for example, on a sensor head of the potentiometric sensor, can be screwed-in. Usually, the sensor head has a greater diameter than the sensor shaft, so that, between these, there is a radial step, which serves as a sensor-head-side, stop surface. The stop surface can serve either itself as a first clamping surface, with which the first sealing ring is pressed against the first sealing surface, or it can axially support a first intermediate ring, which has the first clamping surface.

The thread on the sensor head can be either rigidly connected with the sensor head or it can be formed on a sleeve, which is rotatable relative to the sensor head.

The second seal-seat can include, for example, a second sealing surface for a sealing ring, which borders on a second end section of the sensor opening and faces such, with the second end section facing away from the first end section. In the second end section of the sensor opening, a thread can be provided, into which a screw sleeve can be screwed-in. The end surface of the screw sleeve can serve either itself as a first clamping surface, with which the second sealing ring is pressed against the second sealing surface, or it can axially press against a second intermediate ring, which has the second clamping surface.

For resisting introduction of undesired torques into the screw-in sleeve for clamping the second sealing ring, the screw-in sleeve has preferably no force fit to the process connection member, or to the process seal. I.e. the process connection member and the screw-in sleeve are separated components, there is no friction fit, or shape-fit, between the screw-in sleeve and the process connection member, and the process seal does not bear against the screw-in sleeve.

The first and/or second sealing ring(s) can each be clamped in full-load-bearing arrangement or in incidental-load-bearing arrangement. In incidental-load-bearing arrangement, the seal is loaded only so far, after which other structures make contact to prevent further loading. Clamping with incidental-load-bearing arrangement effects, in each case, a geometrically exactly defined degree of loading of the sealing ring. In the case of clamping in full-load-bearing arrangement, the clamping force can, in contrast, be maximized more easily, to the extent that this is desired.

The exterior surface of the sensor shaft serves likewise as sealing surface for the clamped first and second sealing rings, in order to effect a complete sealing of the annular chamber.

The first and/or second seal-seat(s) can, in an alternative embodiment of the adapter of the invention, each involve an annular groove in the sensor opening. Such annular groove, or grooves, is/are dimensioned such that a sealing ring is clamped between the sensor shaft and the annular groove to such a degree that the resulting surface pressure of the sealing ring, or rings, effects a reliable sealing.

The process connection member can involve, for example, a sleeve surrounding the sensor shaft. Such sleeve surrounds the annular chamber member, at least in an axial section thereof, or is surrounded by the annular chamber member in an axial section, and is secured by suitable engagement means against axial shifting relative to the annular chamber member.

The sleeve can have a thread on its exterior surface or a part of a bayonet engagement, in order to enable assembly into a process opening embodied to be complementary thereto.

Equally, the sleeve can include a flange, for securement to suitable counter-flange.

An end surface of the sleeve or of the annular chamber member facing the process can, at the same time, serve as a clamping surface for a process seal, with the sealing action of the clamped process seal being effected preferably between an abutment surface of the process opening and the exterior surface of the sensor.

The reference feed opening can open, for example, into a connection, for example a tube connection, for a reference liquid line.

The potentiometric sensor can comprise, for example, a pH-sensor or a redox-sensor, especially a so-called single-rod measuring chain, also referred to as a combination electrode. The sensor shaft comprises, for example, glass, metal, or plastic, for example PEEK.

The annular chamber member can, in principle, comprise any material, with plastic, especially PEEK, being currently preferred.

The potentiometric sensor of the invention includes:

An axi-symmetric, sensor shaft, which has a reference liquid opening in its exterior surface, an annular chamber member having an axisymmetric, sensor opening into which the sensor shaft is received in a predetermined axial position relative to the annular chamber member, wherein the sensor opening has a first annular seal against the sensor shaft in a first axial section and a second annular seal against the sensor shaft in a second axial section, the axial position of the reference liquid opening lies between the first and second axial sections, when the sensor shaft is properly placed in the adapter, so that, between the first and second seals and the external surface of the sensor shaft, an annular chamber is formed, which is in communication with the reference liquid opening, and the annular chamber member further includes a duct, which extends between the annular chamber and a reference feed opening, characterized in that the sensor further includes a process connection member having a process connection opening, which surrounds the sensor shaft, and whose axis is aligned with the axis of the sensor opening, wherein the axial position of the process connection member relative to the annular chamber member is fixed, and the process connection member is freely rotatable relative to the annular chamber member.

BRIEF DESCRIPTION OF THE DRAWINGS

The invention will now be described on the basis of the examples of embodiments presented in the drawings, the figures of which show as follows.

DETAILED DISCUSSION

The sensor opening has a first annular seal-seat 2 having a concave, funnel-shaped sealing surface in a first axial section, which borders on the first end section. An annular end surface of the sensor head 4, which surrounds the sensor shaft 10, serves as a first clamping surface, with which a first sealing ring 21 is pressed against the funnel-shaped sealing surface and, due to the resulting radial component of the normal force against the funnel-shaped sealing surface is pressed also against the sensor shaft.

Figure 1:
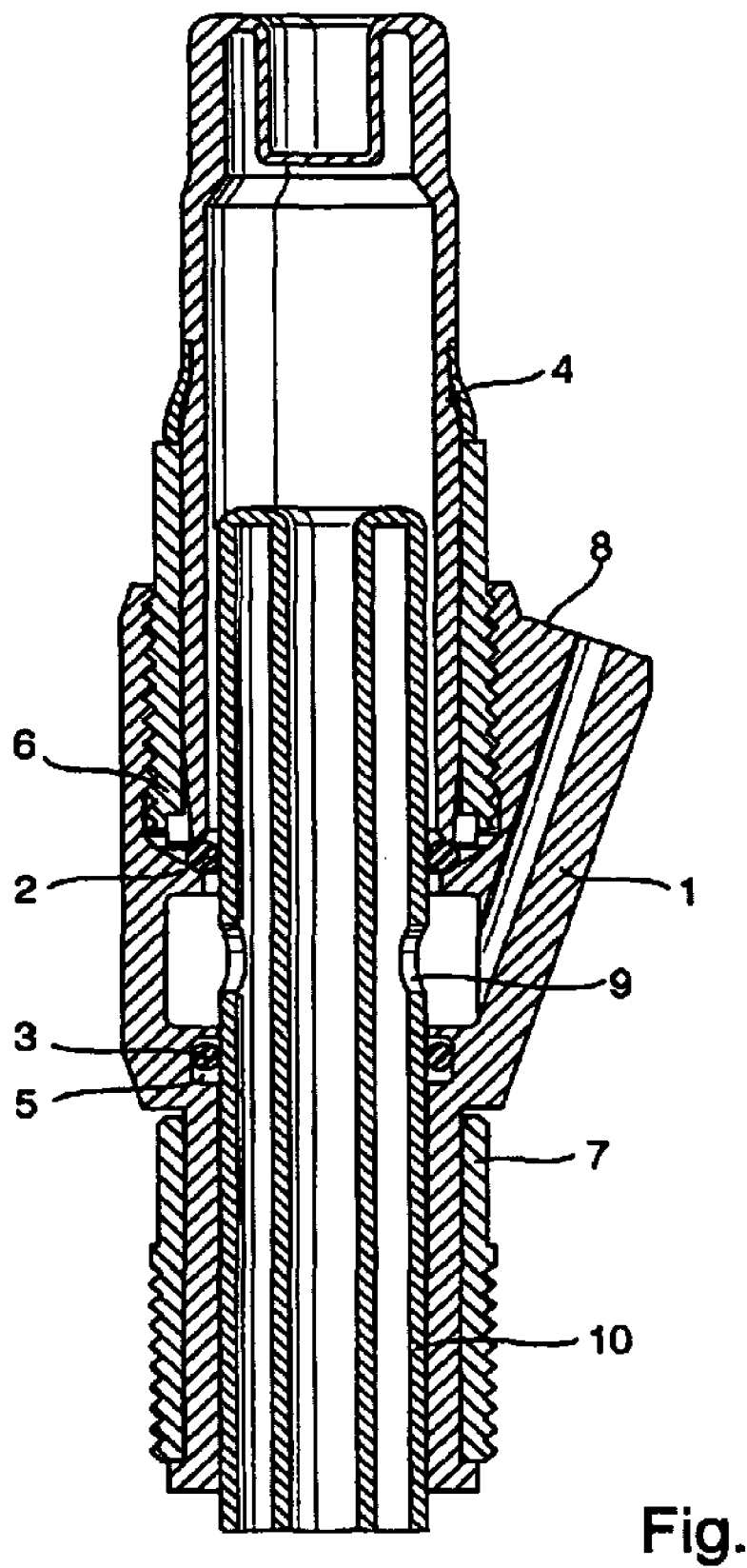
FIG. 1—a longitudinal section through a first example of an embodiment of an adapter of the invention.

The adapter of the invention shown in FIG. 1 includes a annular chamber member 1 having a cylindrical sensor opening, into which a sensor shaft 10 of a pH-sensor is inserted into a predetermined axial position. The axial position is defined by a sensor head 4 of the pH-sensor, which is securely connected with the sensor shaft 10. The sensor head 4 carries a threaded sleeve 6, which is screwed into a thread in a first, end section of the sensor opening.

The sensor opening has a first annular seal-seat 2 having a concave, funnel-shaped sealing surface in a first axial section, which borders on the first end section. An annular end surface of the sensor head, which surrounds the sensor shaft, serves as a first clamping surface, with which a first sealing ring is pressed against the funnel-shaped sealing surface and, due to the resulting radial component of the normal force against the funnel-shaped sealing surface is pressed also against the sensor shaft.

A second seal-seat in a second axial section of the sensor opening includes an annular groove 5, in which a second sealing ring 3 is placed, which is clamped between the floor of the annular groove 5 and the exterior surface of the sensor shaft.

In this way, between the first and second sealing rings, on the one hand, as well as between the exterior surface of the sensor shaft and the wall of the sensor opening, on the other hand, an annular chamber is formed, into which a reference liquid opening 9 in the sensor shaft opens, on the one hand, and a duct 8 opens, on the other hand. Duct 8 extends through the annular chamber member 1 to a reference liquid line connection (not shown). The reference liquid line connection is not shown here in detail.

Annular chamber member 1 is surrounded in its second end section by a cylindrical, threaded sleeve 7, which serves as a process connection member for screwing into a process opening. Threaded sleeve 7 is freely rotatable relative to the annular chamber member 1 and kept, by a radial protrusion on the second end of the annular chamber member 1, from axial shifting relative to the annular chamber member 1. The annular end surface of the annular chamber member 1 on its second end, which surrounds the sensor shaft, serves, at the same time, as a clamping surface for a process seal.

Figure 2:
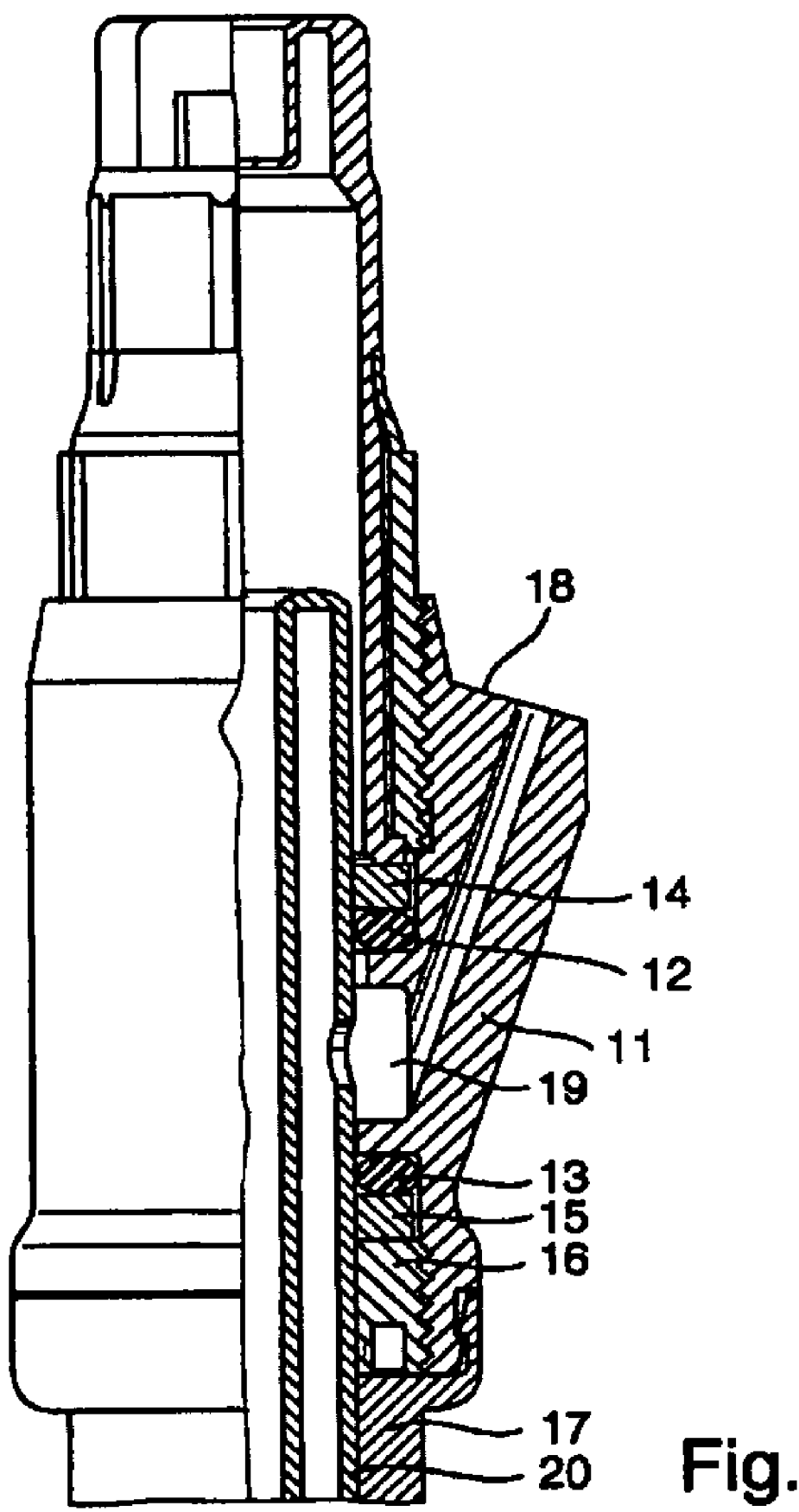
FIG. 2—a longitudinal section through a second example of an embodiment of an adapter of the invention.

The adapter of the invention shown in FIG. 2 includes an annular chamber member 11 having a cylindrical sensor opening, into which a sensor shaft 20 of a pH-sensor is inserted into a predetermined axial position. The axial position is defined by a sensor head of the pH-sensor, which is securely connected with the sensor shaft 10, with the sensor head 4 having a thread, which is screwed into a first end section of the sensor opening.

The sensor opening includes a first annular seal-seat 12 having a concave, ball-bearing-race-shaped, sealing surface in a first axial section, which borders on the first end section. A first clamping ring 14, which contacts the annular end surface of the sensor head, surrounds the sensor shaft, and is freely rotatable relative to the sensor, has a first clamping surface, with which a first sealing ring is pressed against the ball-bearing-race-shaped, sealing surface, and, due to a resulting radial component of the normal force against the sealing surface, against the sensor shaft 20.

A second seal-seat 13 includes a second ball-bearing-race-shaped, sealing surface for a sealing ring. This second sealing surface borders on a second end section of the sensor opening and faces toward it. The second end section faces away from the first end section. In the second end section of the sensor opening, a thread is provided, into which a screw sleeve 16 is screwed. The end surface of the screw sleeve axially supports a second clamping ring 15, which has a second clamping surface, with which a second sealing ring is pressed against the second sealing surface and against the exterior surface of the sensor shaft 20.

In this way, there is formed, between the first and second sealing rings, on the one hand, and between the exterior surface of the sensor shaft 20 and the wall of the sensor opening, on the other hand, an annular chamber, into which, on the one hand, a reference liquid opening 19 in the sensor shaft 20 opens, and, on the other hand, a duct, which extends through the annular chamber member 11 to a reference liquid line connection 18.

The annular chamber member 11 is surrounded in its second end section by a cylindrical, threaded sleeve 17, which serves as process connection member for screwing into a process opening. Threaded sleeve 17 is freely rotatable relative to the annular chamber member 11 and secured by a radial projection on the second end of the annular chamber member 11 against axial shifting relative to the annular chamber member 11. The annular end surface of the threaded sleeve 17, which surrounds the sensor shaft 20, serves as clamping surface for a process seal.

The invention claimed is:

1. An adapter for a potentiometric sensor, comprising:

an axisymmetric sensor shaft, which has a reference liquid opening in its exterior surface;

an annular chamber member having an axisymmetric sensor opening for receiving said axisymmetric sensor shaft in a predetermined axial position relative to said annular chamber member;

said sensor opening having a first annular seal-seat in a first axial section and a second annular seal-seat in a second axial section;

a first sealing ring and a second sealing ring situated between said first seal-seat and said sensor shaft and between said second seal-seat and said sensor shaft, said first and said second sealing rings adapted to be clamped; a process connection member having a process connection opening, which surrounds said sensor shaft, and whose axis is aligned with the axis of said sensor opening; wherein:

the axial position of said reference liquid opening lies between the first and second axial sections, when said sensor shaft is properly positioned in the adapter, so that, between said first and second sealing rings and the exterior surface of said sensor shaft, an annular chamber is formed, which is in communication with said reference liquid opening;

said annular chamber member further having a duct, which extends between said annular chamber and a reference feed opening; and the axial position of said process connection member is fixed relative to said annular chamber member, and the process connection member is freely rotatable relative to said annular chamber member.

2. The adapter as claimed in claim 1, wherein:
said first seal-seat includes a first sealing surface for said first sealing ring, bordering on a first end section of said sensor opening and facing such.

3. The adapter as claimed in claim 2, wherein:
in the first end section of said sensor opening, a thread is provided, into which a complementary thread, provided on a sensor head of the potentiometric sensor, can be screwed-in; and
an annular end surface of said sensor head acts directly or via an intermediate, first clamping ring to press a sealing ring against said first sealing surface.

4. The adapter as claimed in claims 1, wherein:
said second seal-seat includes a second sealing surface for said second sealing ring, which borders on a second end section of said sensor opening and faces such; and
the second end section faces away from the first end section.

5. The adapter as claimed in claim 4, wherein:
in the second end section of said sensor opening, a thread is provided, into which a screw sleeve can be screwed-in, for pressing said second sealing ring against said second sealing surface directly or by means of an interposed, second clamping ring.

6. The adapter as claimed in claim 1, wherein:
the exterior surface of said sensor shaft serves also as a sealing surface for said clamped first and second sealing rings, in order to effect a complete sealing of said annular chamber.

7. The adapter as claimed in claim 1, wherein:
said first and/or said second seal-seat(s) comprise(s) an annular groove in said sensor opening, which is so dimensioned, that a sealing ring is clamped between the sensor shaft and the annular groove to such a degree that the resulting surface pressure of the sealing ring effects a reliable sealing.

8. The adapter as claimed in claim 1, wherein:
said process connection member comprises a sleeve surrounding said sensor shaft;
said sleeve surrounds said annular chamber member, at least in an axial section, or is surrounded by said annular chamber member in an axial section, and is secured by suitable engagement means against axial shifting relative to said annular chamber member.

9. The adapter as claimed in claim 8, wherein:
said sleeve has a thread on its exterior surface, a part of a bayonet coupling, or a flange on its end.

10. The adapter as claimed in claim 8, wherein:
an end surface of said sleeve or annular chamber member facing a process opening serves as clamping surface for a process seal.

11. A potentiometric sensor comprising:
an axisymmetric, sensor shaft, which has a reference liquid opening in its exterior surface;
an annular chamber member having an axisymmetric, sensor opening into which said sensor shaft is received in a predetermined axial position relative to said annular chamber member; and
a process connection member having a process connection opening, which surrounds said sensor shaft, and whose axis is aligned with the axis of said sensor opening, wherein:
said sensor opening has a first annular seal to said sensor shaft in a first axial section and a second annular seal to said sensor shaft in a second axial section;
the axial position of said reference liquid opening lies between said first and said second axial sections, when said sensor shaft is properly placed in said axisymmetric sensor opening, so that, between the first and second seals and the external surface of said sensor shaft, an annular chamber is formed, which is in communication with said reference liquid opening;
said annular chamber member further includes a duct, which extends between said annular chamber and a reference feed opening; and
the axial position of said process connection member relative to the annular chamber member is fixed, and said process connection member is freely rotatable relative to said annular chamber member.

* * * * *